United States Patent [19]

Miyata et al.

[11] Patent Number: 5,527,786
[45] Date of Patent: Jun. 18, 1996

[54] PHOSPHONIC DIESTER DERIVATIVES

[75] Inventors: Kazuyoshi Miyata; Yasuhisa Kurogi; Yoshihiko Tsuda, all of Naruto; Kazuhiko Tsutsumi, Tokushima; Takeshi Iwamoto, Komatsushima; Chieko Naba, Naruto, all of Japan

[73] Assignee: Otsuka Pharmaceutical Factory, Inc., Tokushima, Japan

[21] Appl. No.: 424,345

[22] PCT Filed: Aug. 8, 1994

[86] PCT No.: PCT/JP94/01307

§ 371 Date: Apr. 19, 1995

§ 102(e) Date: Apr. 19, 1995

[87] PCT Pub. No.: WO95/06051

PCT Pub. Date: Mar. 2, 1995

[30] Foreign Application Priority Data

Aug. 20, 1993 [JP] Japan ................................. 5-206259

[51] Int. Cl.$^6$ ..................... A61K 31/675; A61K 31/665; C07F 9/28
[52] U.S. Cl. .................... 514/100; 514/89; 546/24; 549/220
[58] Field of Search ................... 546/24; 549/220; 514/89, 100

[56] References Cited

U.S. PATENT DOCUMENTS

| | | | |
|---|---|---|---|
| 4,232,010 | 11/1980 | Tsukamoto et al. | 546/21 |
| 4,434,162 | 2/1984 | Tsukamoto et al. | 514/79 |
| 4,822,780 | 4/1989 | Tsuda et al. | 514/79 |
| 4,870,199 | 9/1989 | Chen et al. | 556/437 |
| 4,971,957 | 11/1990 | Tsutsumi et al. | 514/79 |
| 5,081,112 | 1/1992 | Tsutsumi et al. | 514/119 |

FOREIGN PATENT DOCUMENTS

| | | |
|---|---|---|
| 0402033 | 12/1990 | European Pat. Off. . |
| 150698 | 9/1982 | Japan . |
| 243888 | 8/1992 | Japan . |
| 43589 | 2/1993 | Japan . |
| 9670 | 1/1994 | Japan . |

OTHER PUBLICATIONS

Chem. Abst. 123: 169894 (1995) (abstract of WO/9506051).
Derwent Abstract of JP A 6–9670, published Jan. 18, 1994.
Derwent Abstract of JP A 5–43589, published Feb. 23, 1993.
Derwent Abstract of JP A 4–24388, published Aug. 31, 1992.
Derwent Abstract of U.S. Patent 4,870,199 (Sep. 1989).
Derwent Abstract of JP 57–150698, published Sep. 17, 1982.
Derwent Abstract of European Journal of Medicine Chemistry, vol. 28, No. 7–8, pp. 539–546 (1993).
Derwent Abstract of JP A 2–11590.
Derwent Abstract of JP A 3–236394.
Derwent Abstract of JP A 4–243888.
Derwent Abstract of JP A 4–244090.
Derwent Abstract of JP 4–356495.
Derwent Abstract of JP 4–43589.
Derwent Abstract of JP 5–97883.

Primary Examiner—Cecilia Tsang
Attorney, Agent, or Firm—Sughrue, Mion, Zinn, Macpeak & Seas

[57] ABSTRACT

The present invention provides a phosphonic diester derivative of the formula:

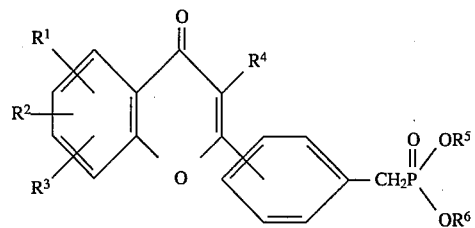

wherein $R^1$, $R^2$ and $R^3$ are the same or different and they each represent a hydrogen atom, a lower alkyl group, a halogen atom, a cyano group, a hydroxyl group, or a lower alkoxy group optionally having a halogen atom, a phenyl group or a hydroxypiperidino group as a substituent; $R^4$ represents a hydrogen atom, a lower alkoxy group, a halogen atom, or a lower alkyl group optionally having a halogen atom or a cyano group as a substituent; and $R^5$ and $R^6$ are the same or different and they each represent a hydrogen atom or a lower alkyl group.

The derivative of the present invention has excellent hypolipidemic, vasodepressor and hypoglycemic activities and is useful as therapeutic and preventive agents for hyperlipidemic diseases, hypertension and diabetes.

8 Claims, No Drawings

PHOSPHONIC DIESTER DERIVATIVES

TECHNICAL FIELD

The present invention relates to novel phosphonic diester derivatives.

PRIOR ART

The phosphonic diester derivatives of the invention are novel compounds not heretofore described in the literature.

DISCLOSURE OF THE INVENTION

The object of the invention is to provide compounds of value as medicines as will be described hereinafter.

The present invention provides a phosphonic diester derivative of the following general formula (1):

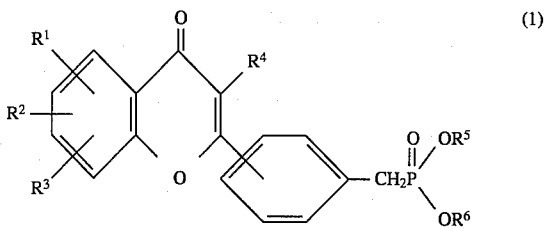

wherein $R^1$, $R^2$ and $R^3$ are the same or different and they each represent a hydrogen atom, a lower alkyl group, a halogen atom, a cyano group, a hydroxyl group, or a lower alkoxy group optionally having a halogen atom, a phenyl group or a hydroxypiperidino group as a substituent; $R^4$ represents a hydrogen atom, a lower alkoxy group, a halogen atom, or a lower alkyl group optionally having a halogen atom or a cyano group as a substituent; and $R^5$ and $R^6$ are the same or different and they each represent a hydrogen atom or a lower alkyl group.

Each of the groups relevant to the above general formula (1) includes the following exemplary species.

The lower alkyl group includes straight- or branched-chain lower alkyl groups such as methyl, ethyl, propyl, isopropyl, butyl, isobutyl, tert-butyl, pentyl, hexyl and so on.

The lower alkyl group optionally having a halogen atom or a cyano group as a substituent includes not only the above-mentioned lower alkyl groups but also bromomethyl, chloromethyl, iodomethyl, 1-bromoethyl, 1-bromopropyl, 1-bromobutyl, 1-bromopentyl, 1-bromohexyl, cyanomethyl, 1-cyanoethyl, 1-cyanopropyl, 1-cyanobutyl, 1-cyanopentyl, 1-cyanohexyl, and the like.

The lower alkoxy group includes methoxy, ethoxy, propoxy, butoxy, pentyloxy, hexyloxy and so on.

The lower alkoxy group optionally having a halogen atom, a phenyl group or a hydroxypiperidino group as a substituent includes not only the above-mentioned lower alkoxy groups but also benzyloxy, 2-phenylethoxy, 3-phenylpropoxy, 4-phenylbutoxy, 5-phenylpentyloxy, 6-phenylhexyloxy, chloromethoxy, bromomethoxy, 2-chloroethoxy, 3-chloropropoxy, 4-chlorobutoxy, 5-chloropentyloxy, 6-chlorohexyloxy, 4-hydroxypiperidinomethoxy, 3-hydroxypiperidinomethoxy, 2-hydroxypiperidinomethoxy, 2-(4-hydroxypiperidino)ethoxy, 3-(4-hydroxypiperidino)propoxy, 4-(4-hydroxypiperidino)butoxy, 5-(4-hydroxypiperidino)pentyloxy, 6-(4-hydroxypiperidino)hexyloxy, and the like.

The halogen atom includes fluorine, chlorine, bromine and iodine.

The phosphonic diester derivative of the formula (1) according to the invention has excellent hypolipidemic, vasodepressor and hypoglycemic activities and is useful as therapeutic agents for hyperlipidemic diseases, hypertension and diabetes. More specifically, the derivative can treat or prevent various types of diseases (hyperlipidemic diseases) such as hypercholesterolemia, hypertriglyceridemia, hyperphospholipidemia and hyper-free fatty acidemia, hypertension and diabetes.

Suitable phosphonic diester derivatives of the formula (1) according to the invention for the above-mentioned pharmaceutical use include those of the formula (1) wherein $R^2$ and $R^3$ each represent a hydrogen atom.

In particular, preferable are those of the formula (1) wherein $R^1$ represents a hydrogen atom, a lower alkyl group, a halogen atom, a hydroxyl group, or a lower alkoxy group optionally having a halogen atom, a phenyl group or a hydroxypiperidino group as a substituent; $R^4$ represents a hydrogen atom, a lower alkoxy group, or a lower alkyl group optionally having a cyano group as a substituent; and $R^5$ and $R^6$ are the same or different and they each represent a lower alkyl group.

The derivatives of the following formula (1') are particularly preferable.

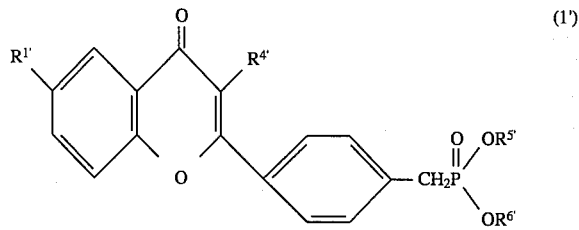

wherein $R^{1'}$ represents a halogen atom or a benzyloxy group; $R^{4'}$ represents a hydrogen atom, a lower alkoxy group or a lower alkyl group; and $R^{5'}$ and $R^{6'}$ are the same or different and they each represent a lower alkyl group.

Among the derivatives of the formula (1'), those of the formula (1') wherein $R^{1'}$ represents a chlorine atom and $R^{4'}$ represents a hydrogen atom or a methyl group are most preferable.

Thus the present invention provides an antidiabetic composition which contains at least one of the phosphonic diester derivatives of the formula (1) or the above-mentioned preferable derivatives as an active ingredient.

Examples of useful compounds as the active ingredient of the antidiabetic composition include derivatives of the formula (1') wherein $R^{1'}$ represents a chlorine atom and $R^{4'}$ represents a hydrogen atom or a methyl group.

The process for preparing the phosphonic diester derivative according to the invention will be described below in detail. The compound can be prepared, for example, by the processes shown in the following Reaction Schemata.

[Reaction Schema-1]

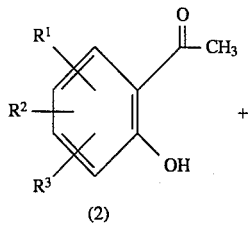

-continued
[Reaction Schema-1]

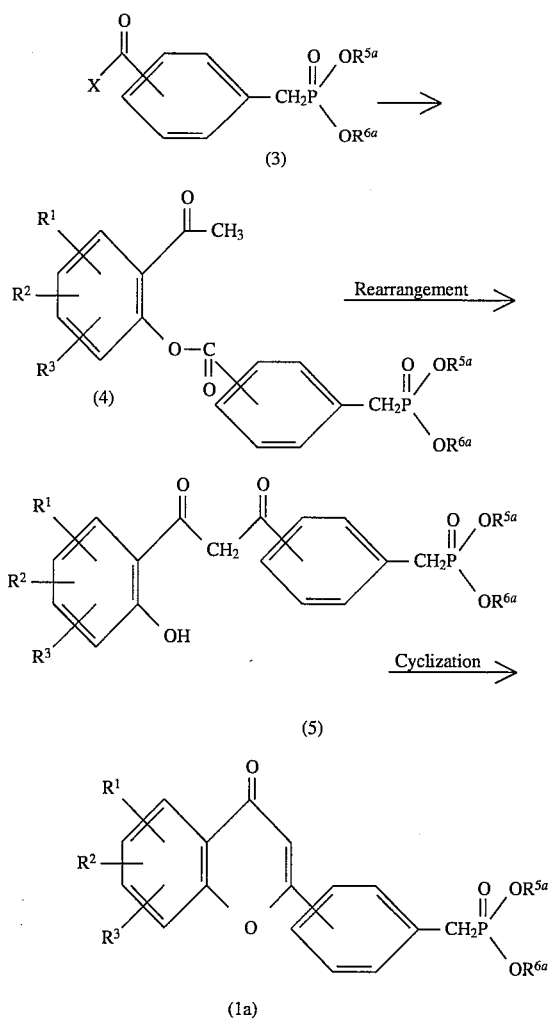

[Reaction Schema-2]

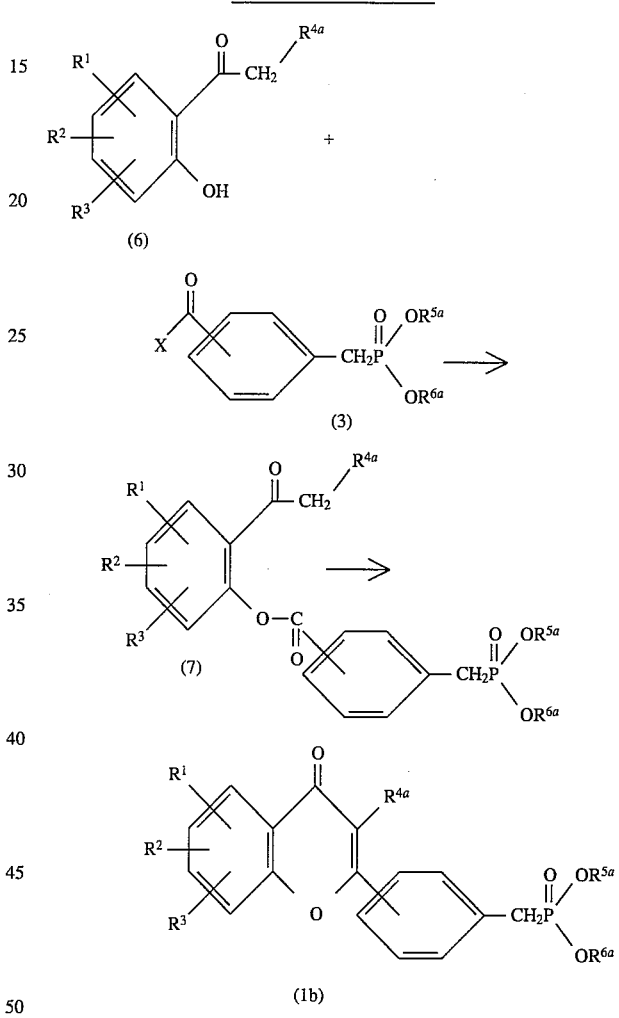

wherein $R^1$, $R^2$ and $R^3$ are as defined above, $R^{5a}$ and $R^{6a}$ each represent a lower alkyl group, and X represents a halogen atom.

The reaction of hydroxyacetophenone derivative (2) with acid halide (3) shown in Reaction Schema-1 can be carried out in the presence of an acid acceptor such as triethylamine, N,N-diethylaniline, pyridine and 4-dimethylaminopyridine in an inert solvent such as dichloromethane, chloroform, carbon tetrachloride, diethylether, and tetrahydrofuran (THF).

The acid halide (3) is preferably used in an approximately equimolar proportion relative to the hydroxyacetophenone derivative (2). The acid acceptor is generally used in an excess proportion relative to the hydroxyacetophenone derivative (2). The reaction goes to completion at 0° C. to room temperature in about 1 to 12 hours.

The rearrangement reaction of the ester (4) thus obtained can be carried out in the presence of 1–3 equivalents of a strong base in a solvent such as pyridine, collidine and lutidine. The strong base is preferably an alkali metal hydroxide such as sodium hydroxide and potassium hydroxide. The reaction temperature is generally selected from the range of room temperature to about 100° C. and the reaction time is generally about 0.5–4 hours.

The reaction product (5) is then treated with a desiccant such as sulfuric acid in an aliphatic carboxylic acid solvent such as acetic acid and propionic acid to provide the compound (1a) of the invention. The reaction generally goes to completion at 0° C. to room temperature in about 0.5–5 hours.

wherein $R^1$, $R^2$, $R^3$, $R^{5a}$, $R^{6a}$ and X are as defined above, and $R^{4a}$ represents a lower alkyl group.

The reaction of compound (6) with acid halide (3) shown in Reaction Schema-2 can be carried out in the same manner as the reaction of hydroxyacetophenone derivative (2) with acid halide (3) shown in Reaction Schema-1.

The resultant ester (7) is subjected to rearrangement reaction in the same way as in Reaction Schema-1, and cyclization reaction follows the desired rearrangement reaction, thereby giving the compound (1b) of the invention.

[Reaction Schema-3]

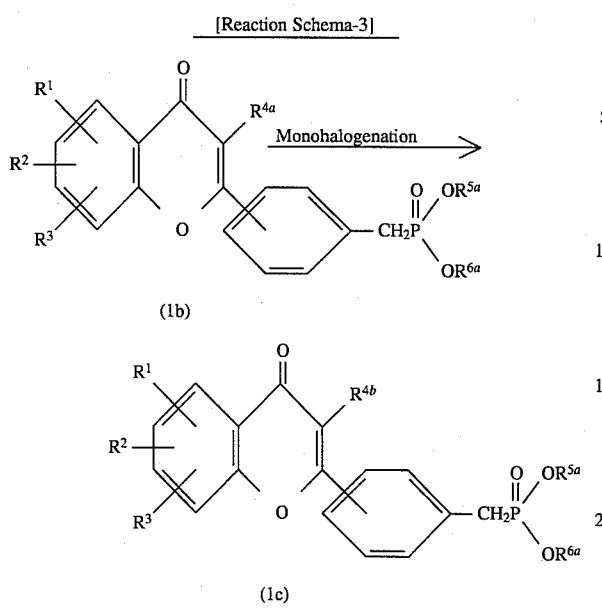

wherein $R^1$, $R^2$, $R^3$, $R^{4a}$, $R^{5a}$ and $R^{6a}$ are as defined above, and $R^{4b}$ represents a halogen-substituted lower alkyl group.

According to the process shown in Reaction Schema-3, the compound (1c) can be prepared by monohalogenating the compound (1b).

The monohalogenation reaction can be carried out using a halogenating agent such as N-bromosuccinimide (NBS), N-chlorosuccinimide (NCS) and bromine in the presence of a catalyst such as benzoyl peroxide, α,α'-azobisisobutyronitrile (AIBN) in an inert solvent such as benzene and carbon tetrachloride. The halogenating agent: is generally used in an amount of about 1 to 1.1 equivalent relative to the compound (1b). The reaction can be carried out at about 50° C. to the reflux temperature of the solvent for about 2–20 hours.

[Reaction Schema-4]

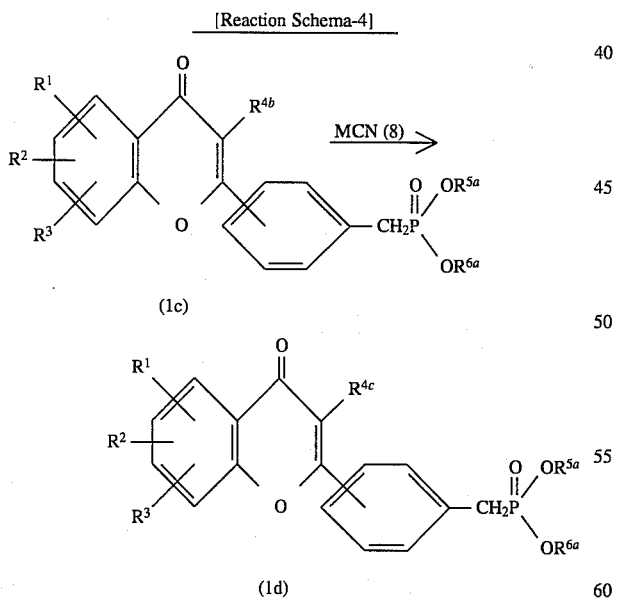

wherein $R^1$, $R^2$, $R^3$, $R^{4b}$, $R^{5a}$ and $R^{6a}$ are as defined above; $R^{4c}$ represents a cyano-substituted lower alkyl group; and M represents an alkali metal.

According to the process shown in Reaction Schema-4, the compound (1d) can be prepared by treating the compound (1c) with an alkali metal cyanide (8) such as sodium cyanide and potassium cyanide in an inert solvent such as methanol, ethanol, dimethylformamide (DMF), dimethyl sulfoxide (DMSO) and an ethanol/water mixture.

The alkali metal cyanide (8) is preferably used in an equimolar to small excess proportion relative to the compound (1c). The reaction goes to completion at room temperature to the reflux temperature of the solvent in about 4–12 hours.

[Reaction Schema-5]

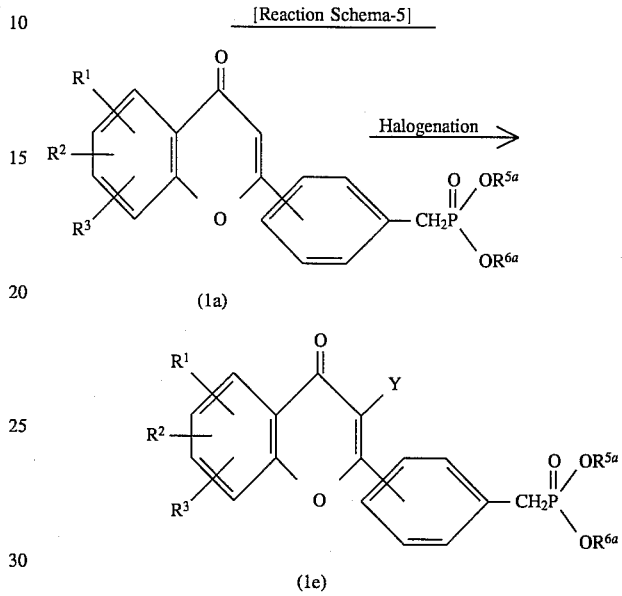

wherein $R^1$, $R^2$, $R^3$, $R^{5a}$ and $R^{6a}$ are as defined above; and Y represents a halogen atom.

The halogenation reaction of the compound (1a) shown in Reaction Schema-5 can be carried out using about 1 to 1.1 equivalent of a halogenating agent such as NBS and NCS in an inert solvent such as acetonitrile, DMF and dimethylacetamide. The reaction goes to completion at 0° C. to room temperature in about 12–24 hours.

[Reaction Schema-6]

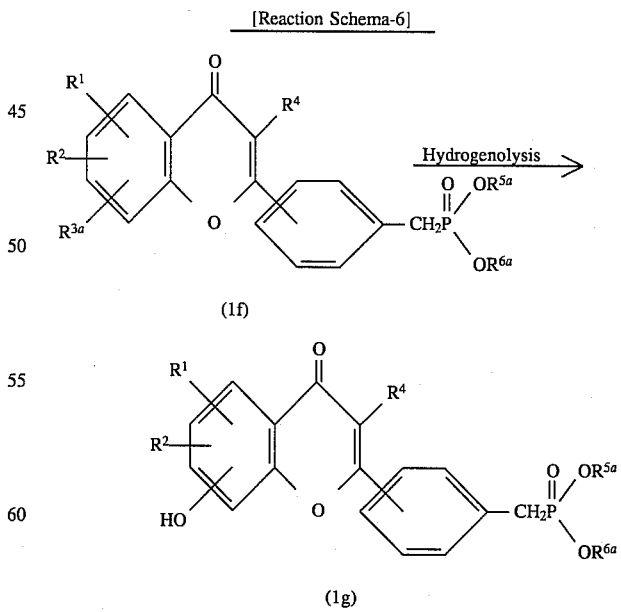

wherein $R^1$, $R^2$, $R^4$, $R^{5a}$ and $R^{6a}$ are as defined above and $R^{3a}$ represents a lower alkoxy group substituted by a phenyl group at the α position.

According to the process shown in Reaction Schema-6, the compound (1g) can be prepared by subjecting the compound (1f) to hydrogenolysis.

The reaction can be carried out by adding hydrogen in the presence of a catalyst such as platinum oxide (IV), platinum black, palladium-containing active carbon and palladium black in an inert solvent such as methanol, ethanol, 1,4-dioxane, acetic acid, ethyl acetate and DMF. This reaction goes to completion at atmospheric pressure and room temperature in about 0.5–3 hours.

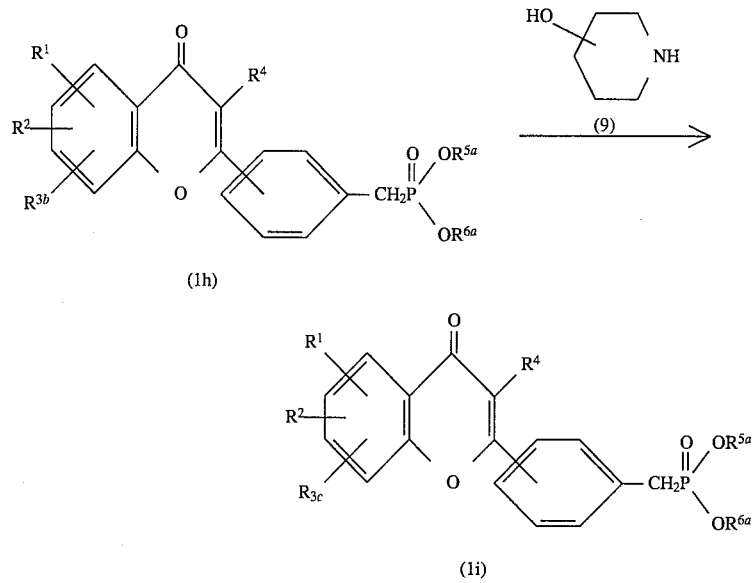

wherein $R^1$, $R^2$, $R^4$, $R^{5a}$ and $R^{6a}$ are as defined above; $R^{3b}$ represents a halogen-substituted lower alkoxy group; $R^{3c}$ represents a hydroxypiperidino-substituted lower alkoxy group.

The reaction of compound (1h) with hydroxypiperidine (9) shown in Reaction Schema-7 can be carried out in the presence of an inorganic base such as sodium hydrogen carbonate, sodium carbonate, potassium hydrogen carbonate and potassium carbonate and an iodide such as sodium iodide and potassium iodide in an inert solvent such as methanol, ethanol, acetonitrile and DMF. The compound (1h) is preferably used in an approximately equimolar proportion relative to the hydroxypiperidine (9). The inorganic base and iodide are generally used in an excess proportion relative to the hydroxypiperidine (9), respectively. The reaction can be carried out at room temperature to the reflux temperature of the solvent for about 1–12 hours.

[Reaction Schema-8]

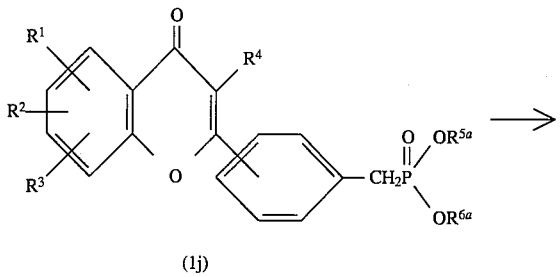

-continued
[Reaction Schema-8]

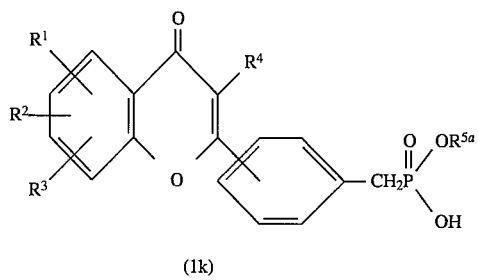

wherein $R^1$, $R^2$, $R^3$, $R^4$, $R^{5a}$ and $R^{6a}$ are as defined above.

According to the process shown in Reaction Schema-8, the objective compound (1k) can be obtained by reacting the compound (1j) with lithium halide such as lithium chloride, lithium bromide and lithium iodide and subsequently treating the reaction mixture with an aqueous solution of mineral acid such as hydrochloric acid and sulfuric acid. The reaction is carried out using an excess amount of lithium halide in an inert solvent such as acetonitrile and DMF at room temperature to the reflux temperature of the solvent for about 5–24 hours.

[Reaction Schema-9]

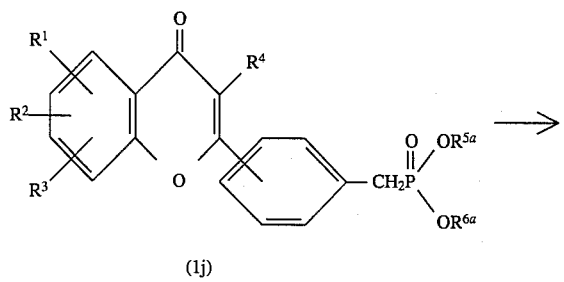

(1j)

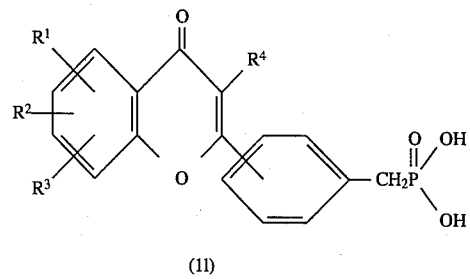

(11)

wherein $R^1$, $R^2$, $R^3$, $R^4$, $R^{5a}$ and $R^{6a}$ are as defined above.

According to the process shown in Reaction Schema-9, the objective compound (11) can be obtained by reacting the compound (1j) with halogenated trialkylsilane such as chlorotrimethylsilane and chlorotriethylsilane and subsequently treating the reaction mixture with an aqueous solution of mineral acid such as hydrochloric acid and sulfuric acid. The reaction is carried out in the presence of an alkali metal iodide such as sodium iodide and potassium iodide in an inert solvent such as acetonitrile and propionitrile. The halogenated trialkylsilane and alkali metal iodide are preferably used in an amount of at least two moles per mole of the compound (1j), respectively. The reaction goes to completion at room temperature to the reflux temperature of the solvent in about 2–12 hours.

[Reaction Schema-10]

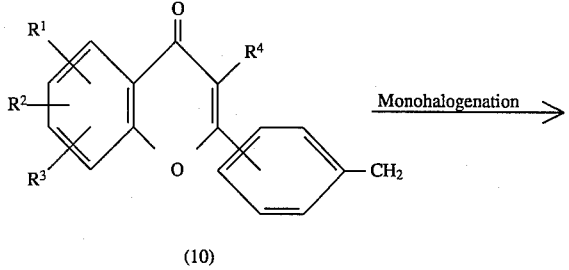

(10)

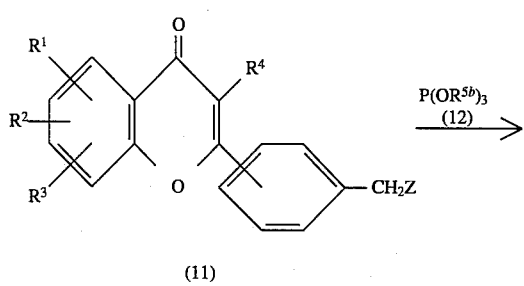

(11)

-continued
[Reaction Schema-10]

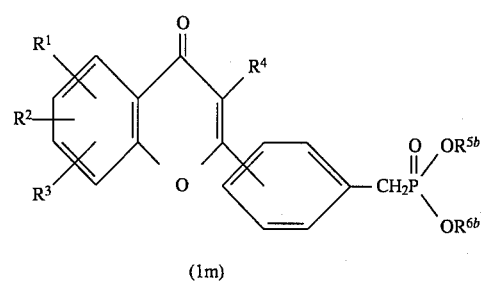

(1m)

wherein $R^1$, $R^2$ and $R^3$ are as defined above; $R^{4d}$ represents a lower alkoxy group; $R^{5b}$ represents a lower alkyl group; $R^{6b}$ represents the same group as $R^{5b}$; and Z represents a halogen atom.

The monohalogenation reaction of compound (10) shown in Reaction Schema-10 can be carried out in the same manner as the monohalogenation of the compound (1b) in Reaction Schema-3. The compound (11) thus obtained can be converted to the compound (1m) of the invention by reacting the compound (11) with trialkyl phosphite (12).

The conversion reaction is preferably carried out without using any solvent, though it can be done in an inert solvent, e.g. lower alcohols such as methanol and ethanol, aromatic hydrocarbons such as benzene, toluene and xylene, and DMF. The trialkyl phosphite (12) is used in an equimolar to excess proportion relative to the compound (11). The reaction can be generally carried out at 100°–180° C. for about 0.5–3 hours, which may slightly vary according to the compound (11).

The starting compound (10) in Reaction Schema-10 can be prepared, for example, by the process shown in the following Reaction Schema-11.

[Reaction Schema-11]

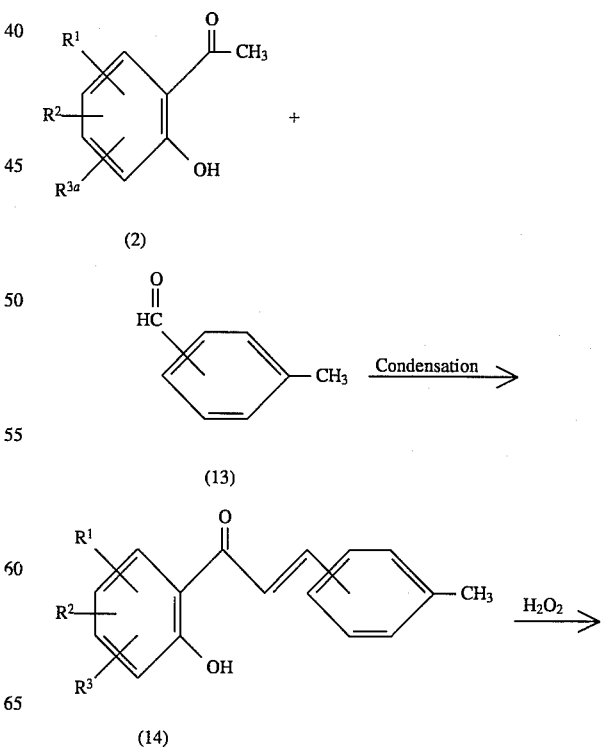

-continued
[Reaction Schema-11]

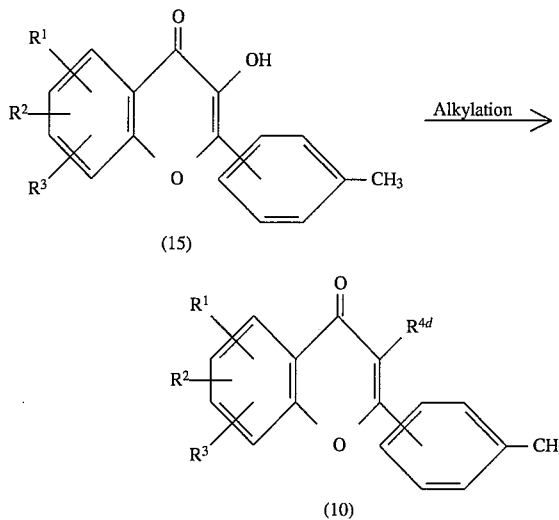

wherein $R^1$, $R^2$, $R^3$ and $R^{4d}$ are as defined above.

The condensation reaction of hydroxyacetophenone derivative (2) with tolualdehyde (13) shown in Reaction Schema-11 can be carried out in the presence of a strong base in a lower alcohol such as methanol and ethanol or a lower alcohol/water mixture. The strong base is preferably an alkali metal hydroxide such as sodium hydroxide and potassium hydroxide, and used in an excess proportion relative to the hydroxyacetophenone derivative (2). The reaction goes to completion at 0° C. to room temperature in about 2–6 hours.

Without isolation or purification, the resultant chalkone derivative (14) can be subjected to the subsequent reaction in the same reactor. More specifically, an aqueous hydrogen peroxide solution is added to the reaction mixture at 0° C. to room temperature and allowed to react for about 7–16 hours, thus giving the compound (15). The compound (15) thus obtained is alkylated to provide the desired starting compound (10). The alkylation reaction can be carried out using one equivalent to an excess amount of an alkyl halide and one equivalent to a small excess amount of a strong base in the presence of an inert solvent such as THF, 1,4-dioxane, 1,2-dimethoxyethane and DMF or a mixture thereof. Examples of the alkyl halide are methyl iodide, ethyl iodide, propyl iodide, butyl iodide, pentyl iodide, hexyl iodide, methyl bromide and ethyl bromide. Examples of the strong base are sodium hydride, potassium hydride and sodium. The reaction goes to completion at room temperature to the reflux temperature of the solvent in about 12–48 hours.

The objective compound in each of the above processes can be easily isolated and purified by conventional separation procedures. Such procedures include adsorption chromatography, preparative thin-layer chromatography, solvent extraction, recrystallization and so on.

Using suitable non-toxic pharmaceutically acceptable carriers, the phosphonic diester derivative of the invention is made in.o pharmaceutical compositions for use. Useful pharmaceutically acceptable carriers include various conventional diluents or excipients such as fillers, volume builders, binders, humectants, disintegrators, surfactants, lubricants, etc. and are selectively employed according to the desired unit dosage form.

The above pharmaceutical composition can be provided in a variety of unit dosage forms according to the intended medical treatment. Typical examples are tablets, pills, powders, solutions, suspensions, emulsions, granules, capsules, suppositories, and injections (solutions, suspensions, etc.).

The molding of tablets can be made using, as said pharmaceutically acceptable carriers, an excipient such as lactose, sucrose, sodium chloride, glucose, urea, starch, calcium carbonate, kaolin, crystalline cellulose, silicic acid, potassium phosphate, etc., a binder such as water, ethanol, propanol, simple syrup, glucose syrup, starch solution, gelatin solution, carboxymethyl cellulose, hydroxypropyl cellulose, methyl cellulose, polyvinylpyrrolidone, etc., a disintegrator such as carboxymethyl cellulose sodium, carboxymethyl cellulose calcium, low-substituted hydroxypropyl cellulose, dry starch, sodium alginate, agar powder, laminaran powder, sodium hydrogen carbonate, calcium carbonate, etc., a surfactant such as polyoxyethylene sorbitan fatty acid ester, sodium lauryl sulfate, stearyl monoglyceride, etc., a disintegration inhibitor such as sucrose, stearin, cacao butter, hydrogenated oil, etc., an absorption promoter such as quaternary ammonium base, sodium lauryl sulfate, etc., a humectant such as glycerin, starch, etc., an adsorbent such as starch, lactose, kaolin, bentonite, colloidal silica, etc., and a lubricant such as purified talc, salts of stearic acid, boric acid powder, polyethylene glycol and so on. Furthermore, such tablets can be coated, if necessary, to provide sugar-coated tablets, gelatin-coated tablets, enteric tablets, film-coated tablets, etc. or be processed into double-layer or multiple-layer tablets.

In the manufacture of pills, various excipients such as glucose, lactose, starch, cacao butter, hydrogenated vegetable oil, kaolin, talc, etc., binders such as gum arabic powder, tragacanth powder, gelatin, ethanol, etc. and disintegrators such as laminaran, starch, etc. can be employed as the pharmaceutically acceptable carrier.

The suppositories can be manufactured using polyethylene glycol, cacao butter, higher alcohols or their esters, gelatin, semisynthetic glycerides, etc. as the carrier.

The capsules can be manufactured in the conventional manner by blending the active ingredient compound of the invention with any of the various pharmaceutically acceptable carriers mentioned above and filling the resulting composition into hard gelatin capsule shells, soft capsule shells or the like.

When the compound of the invention is to be provided in an injectable form such as a solution, emulsion or suspension, the preparation is preferably sterilized and rendered isotonic with respect to the blood. As the diluent for use in such a preparation, water, ethyl alcohol, macrogol, propylene glycol, ethoxylated isostearyl alcohol, polyoxy-isostearyl alcohol, polyoxyethylene sorbitan fatty acid ester, etc. can be employed. In this operation, a sufficient amount of sodium chloride, glucose or glycerin may be added to the composition to provide an isotonic solution. Conventional solubilizers, buffers, local anesthetics, etc. can be also added.

Further, coloring agents, preservatives, perfumes, flavors, sweeteners, or other pharmaceutical compositions can be optionally incorporated in the pharmaceutical compositions of the present invention.

There is no particular limitation on the administration method for the pharmaceutical composition of the invention. Thus, the proper method can be determined according to the particular dosage form, patient's age, sex and other characteristics, severity of disease and other conditions. For example, said tablets, pills, solutions, suspensions, emulsions, granules and capsules are administered by the oral route. The injections are administered singly or in admixture with glucose, amino acid or like conventional infusions by the intravenous route or, if necessary, administered singly by the intramuscular, intradermal, subcutaneous or intraperitoneal route. The suppositories are administered intrarectally.

The proportion of the active ingredient compound of the formula (1) in the pharmaceutical composition of the invention is not critical but can be liberally selected from a broad range. It is generally preferable that the compound accounts for about 1 to 70 weight % of the final composition. The dosing amount of the pharmaceutical composition can be selected according to the selected administration method, patient's age, sex and other characteristics, severity of disease and other conditions. The dosage of the compound of the invention as the active ingredient is preferably about 0.05–100 mg per kg body weight a day and this amount can be administered in 1 to 4 divided doses.

BEST MODE FOR PRACTICING THE INVENTION

Preparation Examples for the compound of the invention are given below as Examples to clarify the invention in further detail.

Example 1

Preparation of diethyl 4-(6-fluoro-4H-1-benzopyran-4-on-2-yl)benzylphosphonate

A 19.0 g quantity of 4-[(diethoxyphosphoryl)methyl]benzoyl chloride was dissolved in 65 ml of dry dichloromethane. A 65 ml portion of a pyridine solution containing 10.0 g of 5'-fluoro-2'-hydroxyacetophenone was slowly added dropwise to the mixture with stirring under ice-cooling. The stirring was continued at room temperature for 12 hours. After addition of 100 ml of water, the reaction mixture was extracted with chloroform. The chloroform layer was washed serially with 250 ml of a 10% aqueous HCl solution and 200 ml of water and dried over Glauber's salt. The solvent was distilled off under reduced pressure, and the residue thus obtained was dissolved in 65 ml of pyridine. A 5.4 g quantity of potassium hydroxide was added to the solution with stirring at room temperature, and the reaction mixture was heated at 50° C. with stirring for 2 hours. After addition of 100 ml of a 10% aqueous HCl solution, the reaction mixture was extracted with chloroform. The chloroform layer was washed with 200 ml of water and dried over Glauber's salt. The solvent was distilled off under reduced pressure and the crude crystals thus obtained were recrystallized from diethylether-n-hexane to provide 15.7 g of diethyl 4-[3-(5-fluoro-2-hydroxyphenyl)-1,3-dioxopropyl]benzylphosphonate as crystals.

A 5.1 g quantity of the crystals thus obtained was dissolved in 16 ml of acetic acid, and 1.2 ml of concentrated sulfuric acid was added thereto at room temperature and stirred for 1 hour. The reaction mixture was added to 200 ml of a 2N aqueous sodium hydroxide solution and extracted with chloroform. The chloroform layer was washed with 100 ml of water and dried over Glauber's salt. The solvent was distilled off under reduced pressure and the crude crystals thus obtained were recrystallized from dichloromethane-n-hexane to provide 3.1 g of the title compound as colorless crystals. Table 1 shows the structure and physical property of the compound obtained.

Examples 2–19

The compounds set forth in Table 1 were prepared in the same manner as in Example 1. Table 1 also shows the structures and physical properties of these compounds.

Example 20

Preparation of dimethyl 4-(6-chloro-3-methyl-4H-1-benzopyran-4-on-2-yl)benzylphosphonate A 39.4 g quantity of 4-[(dimethoxyphosphoryl)methyl] benzoyl chloride was dissolved in 150 ml of dry dichloromethane. Then 150 ml of a pyridine solution containing 27.7 g of 5'-chloro-2'-hydroxypropiophenone was slowly added dropwise to the reaction mixture with stirring under ice-cooling, and the stirring was continued at room temperature for 10 hours. After addition of 150 ml of water, the reaction mixture was extracted with chloroform. The chloroform layer was washed serially with 300 ml of a 10% aqueous HCl solution and 200 ml of water and dried over Glauber's salt. The solvent was distilled off under reduced pressure, and the residue thus obtained was dissolved in 150 ml of pyridine. A 14.0 g quantity of potassium hydroxide was added to the solution with stirring at room temperature, and the mixture was heated at 50° C. with stirring for 2 hours. After addition of 300 ml of a 10% aqueous HCl solution, the reaction mixture was extracted with chloroform. The chloroform layer was washed with 100 ml of water and dried over Glauber's salt. The solvent was distilled off under reduced pressure and the residue was subjected to silica gel column chromatography (eluent: chloroform:ethyl acetate=1:1). The resulting crude crystals were recrystallized from dichloromethane-n-hexane to provide 3.9 g of the title compound as colorless crystals. Table 1 shows the structure and physical property of the compound obtained.

Examples 21 and 22

The compounds set forth in Table 1 were prepared in the same manner as in Example 20. Table 1 also shows the structures and physical properties of these compounds.

Example 23

Preparation of diethyl 4-(3-bromomethyl-6-chloro-4H-1-benzopyran-4-on-2-yl)benzylphosphonate A 3.42 g quantity of the compound obtained in Example 22, 1.5 g of NBS and 50 mg of benzoyl peroxide were suspended in 50 ml of carbon tetrachloride and refluxed with heating for 12 hours. After addition of 50 ml of water, the reaction mixture was extracted with dichloromethane. The dichloromethane layer was washed serially with 50 ml of water and 50 ml of brine and dried over Glauber's salt. The solvent was distilled off under reduced pressure and the residue was purified by silica gel column chromatography (eluent: chloroform:ethyl acetate=1:1) to provide 2.0 g of the title compound as oil. Table 1 shows the structure and physical property of the compound obtained.

Example 24

Preparation of diethyl 4-(6-chloro-3-cyanomethyl-4H-1-benzopyran-4-on-2-yl)benzylphosphonate A 2.0 g quantity of the compound obtained in Example 23 was dissolved in a mixture of 5 ml of ethanol and 0.6 ml of water. After addition of 0.48 g of sodium cyanide with stirring at room temperature, the reaction mixture was refluxed with heating for 12 hours. After addition of 20 ml of water, the reaction mixture was extracted with ethyl acetate. The ethyl acetate layer was washed serially with 20 ml of water and 20 ml of brine and dried over Glauber's salt. The solvent was distilled off under reduced pressure and the residue was subjected to silica gel column chromatography (eluent: chloroform:ethyl acetate=1:1). The resulting crude crystals were recrystallized from dichloromethane-n-hexane to provide 1.0 g of the title compound as colorless crystals. Table 1 shows the structure and physical property of the compound obtained.

Example 25

Preparation of diethyl 4-(7-benzyloxy-3-chloro-4H-1-benzopyran-4-on-2-yl)benzylphosphonate A 2.9 g quantity of the compound obtained in Example 12 was dissolved in 10 ml of DMF. Then 10 ml of a DMF solution containing 0.8 g of NCS was slowly added thereto dropwise with stirring at room temperature. The stirring was continued at room temperature for 12 hours, and 50 ml of water was added to the reaction mixture. The crystals precipitated were collected by filtration and washed with 50 ml of water twice. The crude crystals obtained were air-dried and recrystallized from dichloromethane-n-hexane to provide 2.9 g of the title compound as colorless crystals. Table 1 shows the structure and physical property of the compound obtained.

Example 26

Preparation of diethyl 4-(6-hydroxy-4H-1-benzopyran-4-on-2-yl)benzylphosphonate

A 2.0 g quantity of the compound obtained in Example 11 and 0.24 g of 10% palladium-containing active carbon were suspended in 50 ml of ethanol and degassed well with stirring at room temperature. The reaction mixture was stirred at room temperature in hydrogen atmosphere for 5 hours. The insoluble in the reaction mixture was filtered off and the filtrate was concentrated under reduced pressure. The crude crystals thus obtained were recrystallized from ethanol-n-hexane to provide 1.3 g of the title compound as colorless crystals. Table 1 shows the structure and physical property of the compound obtained.

Example 27

The compound set forth in Table 1 was prepared in the same manner as in Example 26. Table 1 also shows the structure and physical property of the compound.

Example 28

Preparation of diethyl 4-[7-{2-(4-hydroxypiperidino)ethoxy}-4H-1-benzopyran-4-on-2-yl]benzylphosphonate A 1.5 g quantity of the compound obtained in Example 9, 0.51 g of 4-hydroxypiperidine, 0.69 g of anhydrous potassium carbonate and 0.56 g of sodium iodide were suspended in 10 ml of DMF and stirred with heating at 80° C. for 12 hours. After addition of 50 ml of water, the reaction mixture was extracted with dichloromethane. The dichloromethane layer was washed serially with 40 ml of water and 40 ml of brine and dried over Glauber's salt. The solvent was distilled off under reduced pressure, and the crude crystals thus obtained were recrystallized from ethanol-n-hexane to provide 0.50 g of the title compound as colorless crystals. Table 1 shows the structure and physical property of the compound obtained.

Example 29

Preparation of ethyl 4-(6-methyl-4H-1-benzopyran-4-on-2-yl)benzylphosphonate

A 1.4 g quantity of the compound obtained in Example 5 and 1.6 g of lithium bromide were suspended in 30 ml of acetonitrile and refluxed with heating for 12 hours. The reaction mixture was allowed to cool at room temperature. The crystals precipitated were collected by filtration, washed twice with 10 ml of acetonitrile, and dissolved in 20 ml of water. A 10 ml portion of a 10% aqueous HCl solution was added thereto with stirring at room temperature and the stirring was continued at room temperature for 10 minutes. The crystals precipitated were collected by filtration and washed with 10 ml of water twice, thus giving 0.85 g of the title compound as colorless crystals. Table 2 shows the structure and physical property of the compound obtained.

Examples 30–32

The compounds set forth in Table 2 were prepared in the same manner as in Example 29. Table 2 also shows the structures and physical properties of these compounds.

Example 33

Preparation of 4-(6-methyl-4H-1-benzopyran-4-on-2-yl)benzylphosphonic acid

A 1.3 g quantity of the compound obtained in Example 5 and 2.9 g of sodium iodide were suspended in 10 ml of acetonitrile. A 2.1 g portion of chlorotrimethylsilane was slowly added dropwise to the suspension with stirring under ice-cooling. The stirring was continued at room temperature for 2 hours and 10 ml of a 10% aqueous HCl solution was added to the reaction mixture. The crystals precipitated were collected by filtration and washed serially with 20 ml of a 10% aqueous sodium thiosulfate solution and 20 ml of water, thus giving 1.0 g of the title compound as colorless crystals. Table 1 shows the structure and physical property of the compound obtained.

Example 34

Preparation of dimethyl 4-(6-chloro-3-methoxy-4H-1-benzopyran-4-on-2-yl)benzylphosphonate A 8.5 g quantity of 5'-chloro-2'-hydroxyacetophenone and 6.0 g of p-tolualdehyde were dissolved in 105 ml of ethanol. Then 17 ml of an aqueous solution containing 10 g of sodium hydroxide was slowly added thereto dropwise and stirred at room temperature for 4 hours. Then 350 ml of ethanol and 17 ml of an aqueous solution containing 3.5 g of sodium hydroxide were added to the reaction mixture, and 8.3 ml of a 30% aqueous hydrogen peroxide solution was further added dropwise slowly and stirred at room temperature for 12 hours. A 10% aqueous HCl solution was added to adjust the reaction mixture to pH 3. The crystals precipitated were collected by filtration and washed serially with 10 ml of water, 5 ml of ethanol and 10 ml of diethyl ether, thus giving 6.0 g of 6-chloro-3-hydroxy- 2-(4-methylphenyl)-4H-1-benzopyran-4-one as crystals.

Then 15 ml of a DMF solution containing 5.0 g of the crystals was slowly added dropwise to 65 ml of a THF suspension containing 0.70 g of 60% (oily) sodium hydride with stirring under ice-cooling and the stirring was continued at room temperature for 2 hours. A 11.6 g portion of methyl iodide was slowly added dropwise to the reaction mixture and stirred at room temperature for 12 hours. The reaction mixture was poured into 200 ml of ice water and extracted with ethyl acetate. The ethyl acetate layer was washed serially with 100 ml of water and 100 ml of a saturated saline solution and dried over Glauber's salt. The solvent was distilled off under reduced pressure and the crude crystals obtained were recrystallized from ethyl acetate-n-hexane, thus giving 4.2 g of 6-chloro-3-methoxy-2-(4-methylphenyl)-4H-1-benzopyran- 4-one as colorless crystals.

A 4.0 g quantity of the crystals, 2.8 g of NBS and 50 mg of benzoyl peroxide were suspended in 30 ml of benzene and refluxed with heating for 10 hours. After addition of 50 ml of water, the reaction mixture was extracted with dichloromethane. The dichloromethane layer was washed serially with 100 ml of water and 100 ml of brine and dried over Glauber's salt. The solvent was distilled off under reduced pressure and the crude crystals thus obtained were recrystallized from dichloromethane-n-hexane to provide 4.4 g of 2-(4-bromomethylphenyl)-6-chloro- 3-methoxy-4H-1-benzopyran-4-one as colorless crystals.

Then 2.0 g of the crystals were suspended in 5 ml of trimethyl phosphite and heated at 160° C. with stirring for 3 hours. Unreacted trimethyl phosphite was distilled off under reduced pressure, and the residue was purified by silica gel column chromatography (eluent: chloroform:ethyl acetate= 1:1). The crude crystals thus obtained were recrystallized from chloroform-n-hexane to provide 1.4 g of the title compound as colorless crystals. Table 1 shows the structure and physical property of the compound obtained.

Example 35

The compound set forth in Table 1 was prepared in the same manner as in Example 34. Table 1 also shows the structure and physical property of the compound.

TABLE 1

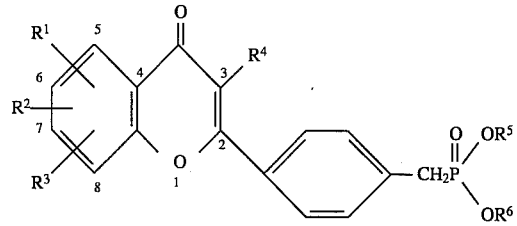

Me = Methyl group, Et = Ethyl group, iPr = Isopropyl group,
nBu = n-Butyl group, tBu = tert-Butyl group, Ph = Phenyl group

| Ex. No. | $R^1$ | $R^2$ | $R^3$ | $R^4$ | $R^5=R^6$ | Mp (°C.) |
|---|---|---|---|---|---|---|
| 1 | 6-F | H | H | H | Et | 147~152 |
| 2 | H | H | H | H | Et | 161~164 |
| 3 | 6-Cl | H | H | H | Et | 155~158 |
| 4 | 6-Br | H | H | H | Et | 166~168 |
| 5 | 6-Me | H | H | H | Et | 143~146 |
| 6 | 6-OMe | H | H | H | Et | 119~122 |
| 7 | 7-OMe | H | H | H | Et | 140~142 |
| 8 | 5-OMe | H | H | H | Et | 110~112 |
| 9 | 7-OCH$_2$CH$_2$Cl | H | H | H | Et | 144~147 |
| 10 | 6-OCH$_2$CH$_2$Cl | H | H | H | Et | 106~109 (decomp.) |
| 11 | 6-OCH$_2$Ph | H | H | H | Et | 119~122 |
| 12 | 7-OCH$_2$Ph | H | H | H | Et | 124~127 |
| 13 | 6-CN | H | H | H | Et | 194.5~196 |
| 14 | 6-Cl | 8-Cl | H | H | Et | 182~186 |
| 15 | 6-F | 8-F | H | H | Et | 177~178 |
| 16 | 5-OMe | 6-OMe | 7-OMe | H | Et | 118~121 |
| 17 | 6-Cl | H | H | H | Me | 161.5~164 |
| 18 | 6-Cl | H | H | H | iPr | 132~133 |
| 19 | 6-Cl | H | H | H | nBu | 130~130.5 |

TABLE 1-continued

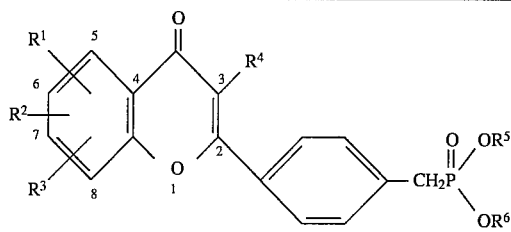

Me = Methyl group, Et = Ethyl group, iPr = Isopropyl group,
nBu = n-Butyl group, tBu = tert-Butyl group, Ph = Phenyl group

| Ex. No. | $R^1$ | $R^2$ | $R^3$ | $R^4$ | $R^5=R^6$ | Mp (°C.) |
|---|---|---|---|---|---|---|
| 20 | 6-Cl | H | H | Me | Me | 181–183 |
| 21 | 6-tBu | H | H | Me | Et | 154–156 |
| 22 | 6-Cl | H | H | Me | Et | 149–151 |
| 23 | 6-Cl | H | H | $CH_2Br$ | Et | Oil (NMR1) |
| 24 | 6-Cl | H | H | $CH_2CN$ | Et | 147.5–148.5 |
| 25 | 7-$OCH_2Ph$ | H | H | Cl | Et | 141–146 |
| 26 | 6-OH | H | H | H | Et | 197.5–199.5 |
| 27 | 7-OH | H | H | H | Et | 176–177.5 |
| 28 | 7-$OCH_2CH_2N\langle\rangle OH$ | H | H | H | Et | 136–140 |
| 33 | 6-Me | H | H | H | H | >250 (NMR2) |
| 34 | 6-Cl | H | H | OMe | Me | 142–144 |
| 35 | 6-Cl | H | H | OMe | Et | 92–95 |

NMR1):

Compound of Example 23 (δ, ppm, $CDCl_3$) 1.29 (t, J=7.3 Hz, 6 H), 3.26 (d, J=22.1 Hz, 2 H), 4.0–4.2 (m, 4 H), 4.47 (s, 2 H), 7.45 (d, J=8.6 Hz, 1 H), 7.64 (dd, J=8.6 Hz, 2.3 Hz, 1 H), 7.84 (d, J=7.9 Hz, 2 H), 8.24 (d, J=2.3 Hz, 1 H)

NMR2):

Compound of Example 33 (δ, ppm, DMSO-$d_6$) 2.43 (s, 3 H), 3.09 (d, J=21.8 Hz, 2 H), 6.98 (s, 1 H), 7.45 (dd, J=7.9 Hz, 1.7 Hz, 2 H), 7.6–7.7 (m, 2 H), 7.83 (s, 1 H), 8.01 (d, J=7.9 Hz, 2 H)

TABLE 2

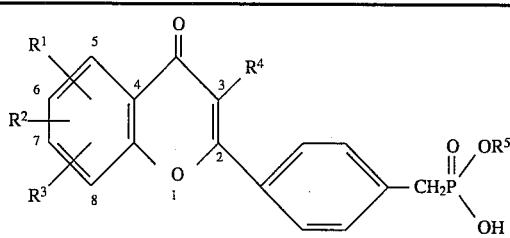

Me = Methyl group, Et = Ethyl group, Ph = Phenyl group

| Ex. No. | $R^1$ | $R^2$ | $R^3$ | $R^4$ | $R^5$ | Mp (°C.) |
|---|---|---|---|---|---|---|
| 29 | 6-Me | H | H | H | Et | 218–219 |
| 30 | 6-Cl | H | H | H | Et | 224–225 |
| 31 | 6-$OCH_2Ph$ | H | H | H | Et | 205–208 |
| 32 | 7-$OCH_2Ph$ | H | H | H | Et | 221–222 |

Given below are Formulation Examples for preparing pharmaceutical compositions which contain the phosphonic diester derivative of the invention as an active ingredient.

Formulation Example 1 Manufacture of tablets

Using the compound obtained in Example 18 as an active ingredient, tablets (1000 tablets) each containing 250 mg of the active ingredient were manufactured according to the following formula.

| Ingredient | Amount (g) |
|---|---|
| Compound of Example 18 | 250 |
| Lactose (product of Japanese pharmacopeia: JP) | 33.5 |
| Corn starch (JP) | 16.5 |
| Carboxymethyl cellulose calcium (JP) | 12.5 |
| Methyl cellulose (JP) | 6.0 |
| Magnesium stearate (JP) | 1.5 |
| Total | 320.0 |

According to the above formula, the compound of Example 18, lactose, corn starch and carboxymethyl cellulose calcium were well blended and granulated using an aqueous solution of methyl cellulose. The granulated mixture was passed through a 24-mesh sieve and the granules under the sieve were mixed with magnesium stearate and compression-molded into tablets.

Formulation Example 2 Manufacture of capsules

Using the compound obtained in Example 3 as an active ingredient, hard gelatin capsules (1000 units) each containing 250 mg of the active ingredient were manufactured according to the following formula.

| Ingredient | Amount (g) |
| --- | --- |
| Compound of Example 3 | 250 |
| Crystalline cellulose (JP) | 30 |
| Corn starch (JP) | 17 |
| Talc (JP) | 2 |
| Magnesium stearate (JP) | 1 |
| Total | 300 |

Thus, according to the above formula, the ingredients were finely pulverized and the powders obtained were blended to give a homogeneous composition. This composition was filled into proper-sized gelatin capsule shells for oral administration to provide the objective capsules.

Formulation Example 3 Manufacture of granules

Using the compound obtained in Example 22 as an active ingredient, granules (1000 g) containing 500 mg of the active ingredient in each gram were manufactured according to the following formula.

| Ingredient | Amount (g) |
| --- | --- |
| Compound of Example 22 | 500 |
| Crystalline cellulose (JP) | 100 |
| Corn starch (JP) | 250 |
| Lactose (JP) | 100 |
| Carboxymethyl cellulose calcium (JP) | 40 |
| Hydroxypropylmethyl cellulose (JP) | 10 |
| Total | 1000 |

Thus, according to the above formula, the compound of Example 22, lactose, corn starch, crystalline cellulose and carboxymethyl cellulose calcium were thoroughly blended and kneaded with an aqueous solution of hydroxypropylmethyl cellulose. The resultant composition was granulated using an extrusion granulator and dried at 50° C. for 2 hours to provide the objective granules.

Given below is Pharmacological Test Example using the derivative of the present invention.

Pharmacological Test Example 1

An experiment for glucose uptake in 3T3L1 cells

3T3L1 cells (CCL-92.1; Dainippon Pharmaceutical Co., Ltd.) were incubated in Dulbecco's modified Eagle medium (Nissui Pharmaceutical Co., Ltd.; code 05919) containing 10% fetal calf serum at 37° C. under 5% $CO_2$. Two days after the cells had grown confluent, 500 μM isobutylmethyl xanthine and 250 μM dexamethasone were added to the medium. The cells were incubated in this medium at 37° C. under 5% $CO_2$ for 2 days, and then in the starting medium which does not contain isobutylmethyl xanthine and dexamethasone at 37° C. under 5% $CO_2$ for 3 days.

Test compounds were dissolved in dimethyl sulfoxide (DMSO) and added to the culture cells such that the final concentration was $10^{-5}$M. The cells were incubated at 37° C. under 5% $CO_2$ for 24 hours. The medium was removed by suction, and Krebs buffer of the following formula was added to the cells. The cells were incubated at 37° C. for 10 minutes. After addition of $^{14}$C-2-deoxyglucose (0.5 μCi/ml), the cells were further incubated at 37° C. for 10 minutes. Krebs buffer (in 1000 ml)

Sodium chloride 6.896 g

Potassium chloride 0.358 g

Magnesium sulfate heptohydrate 0.320 g

N-(2-Hydroxyethyl)piperazine-N'-2-ethane sulfonic acid 2.383 g

A 130 mM aqueous solution of calcium chloride 10 ml

A 8.4% aqueous solution of sodium hydrogen carbonate 10 ml

A 5 g/dl aqueous solution of glucose 1 ml $^{14}$C-2-Deoxyglucose uptake in the cells was assayed. The relative amount of $^{14}$C-2-deoxyglucose uptake in the cells thus prepared using each test compound was determined based on the uptake amount in control cells taken as 1, the control cells being prepared adding test compound-free DMSO alone.

Table 3 shows the results.

TABLE 3

| Test compound | The amount of glucose uptake | Test compound | The amount of glucose uptake |
| --- | --- | --- | --- |
| Example 2 | 1.9 | Example 3 | 5.6 |
| Example 4 | 2.4 | Example 5 | 2.7 |
| Example 6 | 1.9 | Example 7 | 2.2 |
| Example 8 | 1.7 | Example 9 | 2.1 |
| Example 11 | 4.6 | Example 12 | 2.3 |
| Example 17 | 2.1 | Example 18 | 7.1 |
| Example 19 | 2.6 | Example 20 | 2.6 |
| Example 21 | 1.8 | Example 22 | 5.5 |
| Example 24 | 1.9 | Example 26 | 1.6 |
| Example 27 | 1.5 | Example 28 | 1.7 |
| Example 34 | 2.0 | Example 35 | 3.3 |

As clear from Table 3, the compounds of the present invention increase glucose uptake in the cells, thereby lower the amount of glucose in the blood and are effective in treating and preventing diabetes.

We claim:

1. A phosphonic diester compound of the formula:

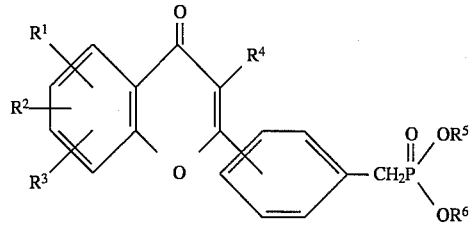

wherein $R^1$, $R^2$ and $R^3$ are the same or different and they each represent a hydrogen atom, a lower alkyl group, a halogen atom, a cyano group, a hydroxyl group, or a lower alkoxy group optionally having a halogen atom, a phenyl group or a 4-hyrdroxypiperdino group as a substituent; $R^4$ represents a hydrogen atom, a lower alkoxy group, a halogen atom, or a lower alkyl group optionally having a halogen atom or a cyano group as a substituent; and $R^5$ and $R^6$ are the same or different and they each represent a hydrogen atom or a lower alkyl group.

2. The phosphonic diester compound of claim 1 which is represented by the formula wherein $R^2$ and $R^3$ each represent a hydrogen atom.

3. The phosphonic diester compound of claim 2 which is represented by the formula wherein $R^1$ represents a hydrogen atom, a lower alkyl group, a halogen atom, a hydroxyl group, or a lower alkoxy group optionally having a halogen atom, a phenyl group or a 4-hyrdroxypiperidino group as a substituent; $R^4$ represents a hydrogen atom, a lower alkoxy group, or a lower alkyl group optionally having a cyano group as a substituent; and $R^5$ and $R^6$ are the same or different and they each represent a lower alkyl group.

4. A phosphonic diester compound of the formula:

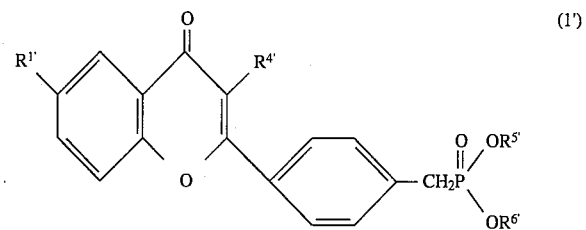

(1')

wherein $R^{1'}$ represents a halogen atom or a benzyloxy group, $R^{4'}$ represents a hydrogen atom, a lower alkoxy group or a lower alkyl group; and $R^{5'}$ and $R^{6'}$ are the same or different and they each represent a lower alkyl group.

5. The phosphonic diester compound of claim 4 which is represented by the formula wherein $R^{1'}$ represents a chlorine atom and $R^{4'}$ represents a hydrogen atom or a methyl group.

6. An antidiabetic composition which comprises the phosphonic diester derivatives claimed in claims 1, 2, 3, 4 or 5 as an active ingredient with a non-toxic pharmaceutically acceptable carrier.

7. The antidiabetic composition of claim 6 wherein the active ingredient is the phosphonic diester derivative claimed in claim 5.

8. A method of treating diabetes which comprises administering to a patient a pharmacologically effective amount of the phosphonic diester derivatives claimed in claims 1, 2, 3, 4 or 5.

* * * * *